US008759575B2

(12) United States Patent
Bösmann et al.

(10) Patent No.: US 8,759,575 B2
(45) Date of Patent: Jun. 24, 2014

(54) METHOD FOR CATALYTICALLY PRODUCING FORMIC ACID

(75) Inventors: Andreas Bösmann, Heßdorf (DE); René Wölfel, Heroldsbach (DE); Peter Wasserscheid, Erlangen (DE); Nicola Taccardi, Uttenreuth (DE); Jakob Albert, Erlangen (DE)

(73) Assignee: JBACH GmbH, Bischberg (DE)

( * ) Notice: Subject to any disclaimer, the term of this patent is extended or adjusted under 35 U.S.C. 154(b) by 0 days.

(21) Appl. No.: 13/823,453

(22) PCT Filed: Aug. 26, 2011

(86) PCT No.: PCT/EP2011/064749
§ 371 (c)(1),
(2), (4) Date: May 29, 2013

(87) PCT Pub. No.: WO2012/034839
PCT Pub. Date: Mar. 22, 2012

(65) Prior Publication Data
US 2013/0245319 A1    Sep. 19, 2013

(30) Foreign Application Priority Data

Sep. 17, 2010  (DE) .......................... 10 2010 045 863
Jun. 8, 2011   (DE) .......................... 10 2011 077 232

(51) Int. Cl.
*C07C 53/02*   (2006.01)
*C07C 51/21*   (2006.01)

(52) U.S. Cl.
USPC .......................................... 562/609; 562/515

(58) Field of Classification Search
CPC ...................................................... C07C 51/23
See application file for complete search history.

(56) References Cited

U.S. PATENT DOCUMENTS 5,695,605  A  * 12/1997  Weinstock et al. ............. 162/79
5,695,606  A    12/1997  Weinstock et al.

OTHER PUBLICATIONS

Bregeault et al, Contes Rendus Academie des Sciences Paris, Une Nouvelle Voie Catalytique pour la Coupure Oxydante des Diols Vicinaux en Presence de Precurseurs au Vanadium, 1989, 309, pp. 459-462.*
Calvo et al., "Formation of Organic Acids during the Hydrolysis and Oxidation of Several Wastes in Sub- and Supercritical Water", Ind. Eng. Chem. Res. 2002, 41, pp. 6503-6509.
International Search Report, issued in PCT/EP2011/064749, dated Jan. 13, 2012.
Jin et al., "Hydrothermal Conversion of Biomass Into Value-Added Products: Technology That Mimics Nature", "Hydrothermal biomass conversion," BioResources 4(2), pp. 704-713, 2009.
Khenkin et al., "Aerobic Oxidation of Vicinal Diols Catalyzed by an Anderson-Type Polyoxometalate, [IMo6O24]5-", Adv. Synth. Catal. 2002, 344, No. 9, pp. 1017-1021.
Khenkin et al., "Oxidative C-C Bond Cleavage of Primary Alcohols and Vicinal Diols Catalyzed by H5PV2Mo10O40 by an Electron Transfer and Oxygen Transfer Reaction Mechanism", J. Am. Chem. Soc. 2008, 130, pp. 14474-14476.
Khenkin et al., "Reaction of Aldehydes with the H5PV2Mo10O40 Polyoxometalate and Cooxidation of Alkanes with Molecular Oxygen", Journal of Catalysis 182, pp. 82-91 (1999).
Niemelä, "The Conversion of Cellulose into Carboxylic Acids by a Drastic Oxygen-Alkali Treatment", Biomass 15 (1988), pp. 223-231.
English language translation of International Preliminary Report on Patentability and Written Opinion of the International Searching Authority for Appl. No. PCT/EP2011/064749 issued Mar. 19, 2013.

* cited by examiner

*Primary Examiner* — Paul A Zucker
(74) *Attorney, Agent, or Firm* — Birch, Stewart, Kolasch & Birch, LLP

(57) ABSTRACT

The invention relates to a method for catalytically producing formic acid. A polyoxometallate ion, which is used as a catalyst, of the general formula $[PMo_xV_yO_{40}]^{5-}$ is brought into contact with an alpha-hydroxyaldehyde, an alpha-hydroxycarboxylic acid, a carbohydrate, or a glycoside in a liquid solution at a temperature below 120° C., wherein $6<x<11$, $1<y<6$, $x+y=12$, and x and y are each a whole number.

19 Claims, No Drawings

METHOD FOR CATALYTICALLY PRODUCING FORMIC ACID

The invention relates to a method for catalytically producing formic acid.

Formic acid has to date been prepared primarily by carbonylation of methanol by means of carbon monoxide, and subsequent hydrolysis of the resultant methyl formate. The methanol released in the course of the hydrolysis is recycled to the first process step. The methanol and carbon monoxide starting materials used in the method are typically obtained from synthesis gas. Synthesis gas is produced generally from natural gas, coal, or petroleum fractions. In the preparation of the methanol for the preparation of formic acid from synthesis gas, and in the carbonylation of the methanol, catalysts are used which have exclusively noble metals as their central atom.

From Jin, F. and Enomoto, H., BioResources 4(2), 2009, pages 704-713, the preparation of acetic acid with a purity between 68.5% and 90% is known, by hydrothermal conversion from rice husks, cellulose starch, and glucose, and the fraction not consisting of acetic acid consists mostly of formic acid. The method employs hydrogen peroxide as oxidizing agent at a temperature of 300° C. under elevated pressure. A disadvantage of this method is that hydrogen peroxide is relatively expensive.

From Niemelä, K., Biomass 15 (1988), pages 223-231, the conversion of cellulose into carboxylic acids is known, using sodium hydroxide at 170 to 190° C. under an oxygen pressure of 200 to 400 kPa. Formic acid is among the carboxylic acids formed in this procedure.

Known from Khenkin, A. M. and Neumann, R., Adv. Synth. Catal. 2002, 344, No. 9, pages 1017-1021 is the $[IMo_6O_{24}]^{5-}$-catalyzed aerobic oxidation of vicinal diols.

Known from U.S. Pat. No. 5,695,606 is a method for oxidative delignification of wood mass and wood fibers. The aim of the oxidative delignification is to oxidize lignin selectively and retain cellulose. The wood mass and wood fibers are contacted in this method with a polyoxometallate, such as $H_5[PV_2Mo_{10}O_{40}]$, for example, under elevated pressure and at elevated temperature. The polyoxometallate is reduced in this method. The method may encompass reoxidization of the polyoxometallate.

Known from Khenkin, A. M. and Neumann, R., J. Am. Chem. Soc. 2008, 130, 14474-14476 is the oxidative cleavage of C-C bonds of primary alcohols and vicinal diols, such as 1,2-ethanediol. The catalyst used in this case is $H_5PV_2Mo_{10}O_{40}$.

Known from Khenkin, A. M., et al., Journal of Catalysis 182, 82-91 (1999) is the reaction of aldehydes with $H_5PV_2Mo_{10}O_{40}$ polyoxometallates. The aldehyde may be, for example, isobutyraldehyde.

It is an object of the present invention to specify an alternative method for producing formic acid.

The invention is achieved through the features of claim 1. Useful embodiments are apparent from the features of claims 2 to 11.

Provided in accordance with the invention is a method for catalytically producing formic acid, wherein a polyoxometallate ion serving as catalyst and of the general formula $[PMo_xV_yO_{40}]^{-5}$ is contacted at a temperature below 120° C. with an alpha-hydroxyaldehyde, an alpha-hydroxycarboxylic acid, a carbohydrate, or a glycoside in a liquid solution, where $6<x<11$ and $1<y<6$, and $x+y=12$, with x and y each being an integer. It is preferred here for the catalyst reduced during the method to be returned to its original state by oxidation. As a result, the method can be carried out in a continuous process.

In the sense of the invention, the term "catalyst" also includes a substance which is altered by oxidation during the method, if after the method it can be returned to its original state by reduction. In this sense, the production of formic acid in accordance with the invention is a catalytic production of formic acid.

The solution may comprise a solvent. The provision of a solvent is not necessary if the alpha-hydroxyaldehyde, alpha-hydroxycarboxylic acid, carbohydrate, or glycoside is already in liquid form. An alpha-hydroxyaldehyde is any molecule in which an OH group is bonded directly to a C atom, the C atom of an aldehyde group also being bonded directly on the C atom. An alpha-hydroxycarboxylic acid is understood to be any molecule in which an OH group is bonded directly to a C atom, the C atom of a carboxyl group also being bonded directly on the C atom. Furthermore, alpha-hydroxyaldehydes and alpha-hydroxycarboxylic acids include all substances which comprise an alpha-hydroxyaldehyde or an alpha-hydroxycarboxylic acid.

The oxidative catalytic production of formic acid from an alpha-hydroxyaldehyde or an alpha-hydroxycarboxylic acid always requires the C-C bond between the aldehyde group or the carboxyl group and the OH-group-bearing C atom to be cleaved. Oxidative catalytic cleavage of this kind was hitherto unknown. Nor does the prior art reveal any indications of an oxidative catalytic cleavage of a C-C bond between the C atom of an aldehyde group or carboxyl group and a C atom bearing an OH group, as required for the formation of formic acid from an alpha-hydroxyaldehyde or an alpha-hydroxycarboxylic acid.

A catalytic cleavage of this kind also occurs when formic acid is produced from carbohydrates or from a glycoside. The oxidative cleavage of adjacent C atoms of a carbohydrate or of the sugar constituent of the glycoside, with an OH group being bonded on at least one of the C atoms, always produces an alpha-hydroxyaldehyde or an alpha-hydroxycarboxylic acid. The C-C bond to the aldehyde group or carboxyl group, said bond being present in these compounds, must always be cleaved in order to produce formic acid.

The method of the invention has the advantage that it permits the production of formic acid from a renewable raw material in an economic way. The increasingly scarce fossil fuels do not have to be used to produce the formic acid. Nor is it necessary first to generate synthesis gas from renewable raw materials. That would entail a considerable cost and complexity, since such raw materials comprise nitrogen compounds and/or sulfur compounds, which would quickly deactivate catalysts having suitable noble metals as their central atom. Such compounds would therefore have to be removed, with cost and complexity, prior to the generation of synthesis gas from renewable raw materials.

In contrast, alpha-hydroxyaldehydes, carbohydrates, and glycosides occur in a large number of renewable raw materials, such as starch, cellulose or hemicellulose, for example. Starch, cellulose, and hemicellulose are produced in large quantities as a product from arable plants or in the course of the industrial pulping of wood, for papermaking, for example.

One of the features of the method of the invention is that the formic acid can be produced directly and with relatively high selectivity from residual substances or raw materials comprising alpha-hydroxyaldehyde, alpha-hydroxycarboxylic acid, carbohydrate, or glycoside. The selectivity may be between 50% and 99%. In particular it has emerged that with the method of the invention, when using oligosaccharides or polysaccharides as carbohydrate, a catalytic conversion takes place with high selectivity without the need for prior hydrolysis to monosaccharides. By selectivity is meant the ratio of the number of moles of C atoms present in total in the formic acid produced in the method to the number of moles of C atoms present in total in the alpha-hydroxyaldehyde, alpha-hydroxycarboxylic acid, carbohydrate, or glycoside starting material employed in the method. Selectivity accordingly is n(HCOOH)/n(C atoms in the starting material).

The reduced catalyst can be oxidized simultaneously with the catalytic production of formic acid or in a separate step of the method, and more particularly may also be oxidized in spatial separation from the oxidation of the alpha-hydroxyaldehyde, alpha-hydroxycarboxylic acid, carbohydrate, or glycoside. As a result optimum conditions in each case, in respect of pressure and temperature, for example, can be selected for the oxidation of the alpha-hydroxyaldehyde, alpha-hydroxycarboxylic acid, carbohydrate, or glycoside and also for the reoxidation of the catalyst. Furthermore, any possible dehydration of molecules containing alpha-hydroxyaldehyde can be diminished. The heat produced during the method of the invention may be utilized by another process, more particularly a process in which the formic acid produced is reacted. Moreover, the formic acid produced in the method may be converted directly into hydrogen and carbon dioxide by means of a heterogeneous catalyst, such as platinum or palladium, for example.

The alpha-hydroxyaldehyde, the alpha-hydroxycarboxylic acid, the carbohydrate, or the glycoside may comprise a monosaccharide, more particularly an aldose, a disaccharide, oligosaccharide, or polysaccharide, starch, cellulose, hemicellulose, glucose, sucrose, xylose, cellobiose, xylan, a heterocligosaccharide, a heteropolysaccharide, glycolic acid, or lactic acid, or a raw material, more particularly a renewable raw material, more particularly an untreated renewable raw material, or residual substances comprising the alpha-hydroxyaldehyde, the alpha-hydroxycarboxylic acid, the carbohydrate, or the glycoside. Untreated here means that it has not been broken down chemically beforehand. The residual substance or the renewable raw material may be a plant, a fungus, or bacteria, or constituents of plants, fungi, or bacteria, wood, more particularly in the form of wood flour or wood chips, paper, more particularly wastepaper, algae, cyanobacteria, or silage. The alpha-hydroxyaldehyde, alpha-hydroxycarboxylic acid, carbohydrate, or glycoside may also comprise a mixture of at least two of the stated substances, or may have formed from at least one of the stated substances or from the mixture.

Many of the stated raw materials are obtained as byproducts, in papermaking or wood processing, for example. Accordingly they are available as favorable starting material for the method of the invention. As a result, the method of the invention can be implemented very cost-effectively. Another contributor to this is the oxidation of the catalyst reduced during the catalyzed reaction (i.e., reoxidation), which allows the catalyst to be used for a very long time.

One embodiment of the method sees the catalyst being oxidized by blown introduction of oxygen or of a gas mixture containing oxygen, more particularly more than 10% by volume, into the solution, or by addition of an oxidizing agent, more particularly $H_2O_2$ or $N_2O$, to the solution. The gas mixture may be, for example, air or synthetic air.

The solution may comprise a polar solvent, more particularly water, formic acid, an ionic liquid, or mixtures of these solvents.

It has proven advantageous if an inorganic acid, more particularly sulfuric acid, phosphoric acid, hydrochloric acid, or carbonic acid, a carboxylic acid, having more particularly 2 to 20 C atoms, or a dicarboxylic acid, having more particularly 2 to 20 C atoms, is added to the solution.

By this means it is possible to accelerate depolymerization of the alpha-hydroxyaldehyde, alpha-hydroxycarboxylic acid, carbohydrate, glycoside, or stated raw materials or residual substances.

Additionally it is possible for a surfactant or other additive, more particularly a sulfonic acid, more particularly methanesulfonic acid, trifluoromethanesulfonic acid, camphorsulfonic acid, toluenesulfonic acid, more particularly para-toluenesulfonic acid, chlorosulfonic acid, xylenesulfonic acid, benzenesulfonic acid, or a derivative of one of said acids, more particularly chlorobenzenesulfonic acid, more particularly para-chlorobenzenesulfonic acid, or a salt of one of said acids or of the derivative, or another substance which in an aqueous solution forms one of said acids or the derivative, to be added to the solution. As a result it is more particularly possible to implement more effective reaction of the residual substances, more particularly wastepaper, and the renewable raw materials, more particularly wood, more particularly in the form of wood flour, and also bacteria, more particularly cyanobacteria. Overall it is possible by this means to achieve a better yield. An advantage of para-chlorobenzenesulfonic acid is that addition thereof does not produce foaming.

The contacting takes place preferably at a temperature of 15 to 120° C., more particularly 50 to 110° C., more particularly 60 to 100° C., more particularly 70 to 95° C., more particularly 85 to 95° C. The higher the temperature, the more rapid the catalytic conversion. At temperatures up to 100° C., the reaction takes place with high selectivity. The more the temperature exceeds 100° C., the greater the fall in the selectivity of the reaction. Contacting at a temperature of not more than 100° C. is therefore advantageous.

It is further proven advantageous for the contacting to take place under an oxygen partial pressure of 1 to 500 bar, more particularly 5 to 150 bar, more particularly 20 to 120 bar, more particularly 30 to 80 bar, more particularly 50 to 75 bar. The higher the oxygen partial pressure, the more rapid the oxidation of the catalyst reduced during the method.

Formic acid produced in the method can be removed from the solution by distillation, reactive distillation, extraction, more particularly together with the catalyst, more particularly by addition of a base, more particularly an amine, by stripping or, after reaction with a heterogeneous catalyst, more particularly platinum or palladium, it may be removed from the solution in the form of reaction products—hydrogen and carbon dioxide—formed during the reaction. In this case the heterogeneous catalyst may take the form, for example, of a wire mesh or of a porous spongelike structure. If catalytic production of formic acid is accompanied by oxidation of the catalyst, the reaction with the heterogeneous catalyst ought not to take place simultaneously with the oxidation of the catalyst, on account of the reactivity of the hydrogen, so as to prevent, for example, a detonating gas reaction. The extraction may also take the form of a reactive extraction.

It is preferred to add an ether, more particularly diisopropyl ether, ethyl tert-butyl ether, ethyl isobutyl ether, ethyl sec-butyl ether, methyl tert-pentyl ether, di-n-propyl ether, ethyl n-butyl ether, ethyl tert-pentyl ether, diisobutyl ether, or di-n-butyl ether, as extractant to the solution for the purpose of extracting the formic acid. It is possible to add to the solution an amide, more particularly N,N-di-n-butylformamide, N-di-n-acetamide, N-methyl-N-heptylformamide, N-n-butyl-N-2-ethylhexylformamide, or N-n-butyl-N-cyclohexylformamide, for the purpose of extracting the formic acid together with the catalyst. The extraction together with the catalyst is especially advantageous when the solution contains the alpha-hydroxyaldehyde, alpha-hydroxycarboxylic acid, carbohydrate, or glycoside in only a low concentration. This may be the case in particular with renewable raw materials, such as algae, for example, of which often only a few percent by weight are present in water.

The invention is elucidated in more detail below by means of working examples.

EXAMPLE 1

Oxidation of glucose in water at 80° C.

Added at room temperature to 100 g of distilled water are 3.30 g of glucose and 1.74 g of $H_5PMo_{10}V_2O_{40}$. The mixture is heated to 80° C. under 30 bar oxygen in a stirred tank autoclave with gas introduction stirrer, and stirred for 7 hours. Following cooling and letdown, the formic acid content of the solution corresponds to a yield of 51%. Other substances are no longer detectable in the reaction solution by means of NMR.

EXAMPLE 2

Oxidation of glucose in water at 70° C.

The reaction is carried out as described for example 1. In deviation from that example, the reaction takes place at 70° C. for 22 hours. The formic acid content of the solution corresponds to a yield of 51%. Other substances are no longer detectable in the reaction solution by means of NMR.

EXAMPLE 3

Oxidation of glucose in water at 90° C.

The reaction is carried out as described for example 1. In deviation from that example, the reaction takes place at 90° C. for 3 hours. The formic acid content of the solution corresponds to a yield of 52%. Other substances are no longer detectable in the reaction solution by means of NMR.

EXAMPLE 4

Product stability under reaction conditions

Added at room temperature to 100 g of distilled water are 4.70 g of formic acid. Added to this solution are 1.74 g of $H_5PMo_{10}V_2O_{40}$. The mixture is heated to 90° C. under 30 bar oxygen in a stirred tank autoclave with gas introduction stirrer, and stirred for 20 hours. After cooling and letdown, the reaction solution yields 4.70 g of formic acid.

EXAMPLE 5

Oxidation of xylose

The reaction is carried out as described for example 1. Instead of the glucose, 3.30 g of xylose are added. The formic acid content of the solution corresponds to a yield of 54%. Other substances are no longer detectable in the solution by means of NMR.

EXAMPLE 6

Oxidation of the hemicellulose xylan

The reaction is carried out as described for example 1. Instead of the glucose, 3.30 g of xylan are added. The formic acid content of the solution corresponds to a yield of 33%.

EXAMPLE 7

Oxidation of cellulose

The reaction is carried out as described for example 1. Instead of the glucose, 3.30 g of cellulose are added and suspended in the water. The reaction time, in deviation from example 1, is 97 hours. The formic acid content of the solution corresponds to a yield of 27%.

EXAMPLE 8

Oxidation of sucrose

The reaction is carried out as described for example 1. Instead of the glucose, 3.30 g of sucrose are added. The formic acid content of the solution corresponds to a yield of 48%. Other substances are no longer detectable in the solution by means of NMR.

EXAMPLE 9

Oxidation of poplar wood

The reaction is carried out as described for example 1. Instead of the glucose, 3.30 g of poplar wood in the form of sawdust are added and suspended in the water. The formic acid content of the solution after a reaction time of 97 hours, based on the mass employed, corresponds to a yield of 19%.

EXAMPLE 10

Oxidation of poplar wood with addition of an additive

The reaction is carried out as described for example 1. Instead of the glucose, 2.70 g of poplar wood in the form of sawdust are added and suspended in the water. In addition, 1.91 g of para-toluenesulfonic acid are added as an additive. The formic acid content of the solution after a reaction time of 24 hours, based on the mass employed, corresponds to a yield of 39%.

EXAMPLE 11

Oxidation with increased amount of catalyst

The reaction is carried out as described for example 1. In deviation therefrom, 7.40 g of $H_5PMo_{10}V_2O_{40}$ are added instead of 1.74 g of $H_5PMo_{10}V_2O_{40}$. The formic acid content of the solution corresponds to a yield of 52%. Other substances are no longer detectable in the solution by means of NMR.

EXAMPLE 12

Oxidation with increased amount of substrate

The reaction is carried out as described for example 1. In deviation therefrom, 10.0 g of glucose are added, instead of 3.30 g of glucose. The reaction time is 51 hours instead of 7 hours. The formic acid content of the solution corresponds to a yield of 49%. Other substances are no longer detectable in the solution by means of NMR.

EXAMPLE 13

Oxidation with increased amount of catalyst and increased amount of substrate

The reaction is carried out as described for example 1. In deviation therefrom, 7.40 g of $H_5PMo_{10}V_2O_{40}$ and 10.0 g of glucose are added. The reaction time is 24 hours instead of 7 hours. The formic acid content of the solution corresponds to a yield of 53%. Other substances are no longer detectable in the solution by means of NMR.

EXAMPLE 14

Oxidation under reduced pressure

The reaction is carried out as described for example 1. In deviation therefrom, the oxidation reaction of glucose takes place at 10 bar of oxygen instead of 30 bar of oxygen. The formic acid content of the solution corresponds to a yield of 49%. Other substances are no longer detectable in the solution by means of NMR.

EXAMPLE 15

Oxidation under increased pressure

The reaction is carried out as described for example 1. In deviation therefrom, the oxidation reaction of glucose takes place at 80 bar of oxygen instead of 30 bar of oxygen. The formic acid content of the solution corresponds to a yield of 51%. Other substances are no longer detectable in the solution by means of NMR.

EXAMPLE 16

Oxidation with air

The reaction is carried out as described for example 1. In deviation therefrom, the oxidation reaction of glucose takes place at 80 bar of air instead of 30 bar of oxygen. The formic acid content of the solution corresponds to a yield of 51%. Other substances are no longer detectable in the solution by means of NMR.

EXAMPLE 17

Oxidation with an oxygen-containing gas mixture

The reaction is carried out as described for example 1. In deviation therefrom, the oxidation reaction of glucose takes place with 60 bar of a mixture of equal volume fractions of oxygen and nitrogen, instead of with 30 bar oxygen. The formic acid content of the solution corresponds to a yield of 53%. Other substances are no longer detectable in the solution by means of NMR.

EXAMPLE 18

Extraction of formic acid

Added to a solution, corresponding to a reaction solution, of 10.0 g of water, 0.174 g of $H_5PMo_{10}V_2O_{40}$, and 5.0 g of formic acid are 5.0 g of di-n-butyl ether as extractant, which is mixed with the aqueous phase. According to visual assessment, the orange-colored catalyst remains completely in the aqueous phase, while the formic acid goes over into the organic phase. The partition coefficient of the formic acid is found by NMR to have a value of 0.81.

EXAMPLE 19

Extraction of formic acid and catalyst

Added to a solution, corresponding to a reaction solution, of 10.0 g of water, 0.174 g of $H_5PMo_{10}V_2O_{40}$, and 5.0 g of formic acid are 5.0 g of N,N-di-n-butylformamide as extractant, which is mixed with the aqueous phase. According to visual assessment, the orange-colored catalyst goes over completely into the organic phase. The partition coefficient of the formic acid is found by NMR to have a value of 1.27.

The invention claimed is:

1. A method for catalytically producing formic acid, wherein a polyoxometallate ion serving as catalyst and of the general formula $[PMo_xV_yO_{40}]^{5-}$ is contacted at a temperature below 120° C. with an alpha-hydroxyaldehyde, an alpha hydroxycarboxylic acid, a carbohydrate, or a glycoside in a liquid solution,
where $6<x<11$ and $1<y<6$, and $x+y=12$, with x and y each being an integer, and
wherein the contacting takes place under an oxygen partial pressure of 1 to 500 bar.

2. The method of claim 1, wherein the catalyst reduced during the method is returned to its original state by oxidation.

3. The method of claim 1, wherein the alpha-hydroxyaldehyde, the alpha-hydroxycarboxylic acid, the carbohydrate, or the glycoside is selected from the group consisting of:
   (i) a monosaccharide, a disaccharide, an oligosaccharide, a polysaccharide, a heterooligosaccharide, and a heteropolysaccharide, or
   (ii) glycolic acid, and lactic acid,
   or a mixture of at least two of the stated substances, or has formed from at least one of the stated substances or from the mixture.

4. The method of claim 1, wherein the catalyst is oxidized by addition of an oxidizing agent to the solution.

5. The method of claim 1, wherein the solution comprises a polar solvent, an ionic liquid, or mixtures of these solvents.

6. The method of claim 1, wherein an inorganic acid, a carboxylic acid, or a dicarboxylic acid is added to the solution.

7. The method of claim 1, wherein a surfactant or other additive, a sulfonic acid, or a derivative thereof, or a salt thereof, or another substance which in an aqueous solution forms a sulfonic acid, is added to the solution.

8. The method of claim 1, wherein the contacting occurs at a temperature of 15 to 120° C.

9. The method of claim 1, wherein the formic acid produced in the method is removed from the solution by distillation, reactive distillation, extraction, by stripping, or after reaction with a heterogeneous catalyst it is removed from the solution in the form of reaction products—hydrogen and carbon dioxide—formed during the reaction.

10. The method of claim 9, wherein an ether is added as extractant to the solution for the purpose of extracting the formic acid, or an amide is added for the purpose of extracting the formic acid together with the catalyst.

11. The method according to claim 4, wherein the oxidizing agent is $H_2O_2$, or $N_2O$.

12. The method according to claim 4, wherein the oxidizing agent is oxygen or a gas mixture containing oxygen.

13. The method according to claim 5, wherein the solution comprises water, formic acid, or mixtures thereof.

14. The method of claim 7, wherein the sulfonic acid is selected from the group of acids consisting of: methanesulfonic acid, trifluoromethanesulfonic acid, camphorsulfonic acid, toluenesulfonic acid, para-toluenesulfonic acid, chlorosulfonic acid, xylenesulfonic acid, benzenesulfonic acid, chlorobenzenesulfonic acid, para-chlorobenzenesulfonic acid or a salt thereof.

15. The method according to claim 6, wherein one or more of acids are added to the solution, and wherein the one or more acids are selected from the group of acids consisting of: acetic acid, propionic acid, butyric acid, valeric acid, caproic acid, oxalic acid, malonic acid, succinic acid, glutaric acid, and adipic acid.

16. The method of claim 10, wherein the ether is selected from the group of ethers consisting of: diisopropyl ether, ethyl tert-butyl ether, ethyl isobutyl ether, ethyl sec-butyl ether, methyl tert-pentyl ether, di-n-propyl ether, ethyl n-butyl ether, ethyl tertpentyl ether, diisobutyl ether, and di-n-butyl ether, and wherein the amide is selected from the group of amides consisting of: N,N-di-n-butylformamide, N-di-n-acetamide, N-methyl-N-heptylformamide, N-n-butyl-N-2-ethylhexylformamide, and N-n-butyl-N-cyclohexylformamide.

17. The method of claim 1, wherein the contacting takes place under an oxygen partial pressure of 5 to 150 bar.

18. The method of claim 1, wherein the alpha-hydroxyaldehyde, the alpha-hydroxycarboxylic acid, the carbohydrate, or the glycoside is selected from the group consisting of: starch, cellulose, hemicellulose, glucose, sucrose, xylose, cellobiose, and xylan.

19. The method of claim 1, wherein the alpha-hydroxyaldehyde, alpha-hydroxycarboxylic acid, carbohydrate, or glycoside are comprised by and contacted with the catalyst in a form of a plant, fungus, bacteria, wood, paper, algae, cyanobacteria or silage.

* * * * *